United States Patent
Cortesi

[11] 4,318,190
[45] Mar. 9, 1982

[54] METAL-INFIBULUM CERAMIC-HEAD ENDOPROSTHESIS

[76] Inventor: Sergio S. Cortesi, Via Guglielmini, 6, Bologna, Italy

[21] Appl. No.: 72,802

[22] Filed: Sep. 5, 1979

[51] Int. Cl.³ .............................................. A61F 1/24
[52] U.S. Cl. ................. 3/1.913; 128/92 CA
[58] Field of Search ................ 3/1.9, 1.91, 1.911, 3/1.912, 1.913; 128/92 C, 92 CA

[56] References Cited

U.S. PATENT DOCUMENTS

| | | | |
|---|---|---|---|
| 3,894,297 | 7/1975 | Mittelmeier et al. | 128/92 CA X |
| 4,012,795 | 3/1977 | Dorre et al. | 3/1.91 |
| 4,058,856 | 11/1977 | Dorre et al. | 3/1.913 X |

FOREIGN PATENT DOCUMENTS

| | | | |
|---|---|---|---|
| 2548077 | 5/1977 | Fed. Rep. of Germany | 3/1.913 |
| 1371335 | 10/1974 | United Kingdom | 3/1.913 |

*Primary Examiner*—Arnold Turk
*Attorney, Agent, or Firm*—Guido Modiano; Albert Josif

[57] ABSTRACT

A hipbone endoprosthesis comprises a metal-infibulum insertable into the femur medullar channel and a ceramic material spherical head associable with a portion of the infibulum provided for projecting from the medullar channel.

The projecting portion is provided with a cylindrical shank having a reduced diameter portion whereat are formed axially extending annular ridges for coupling with the spherical head.

3 Claims, 1 Drawing Figure

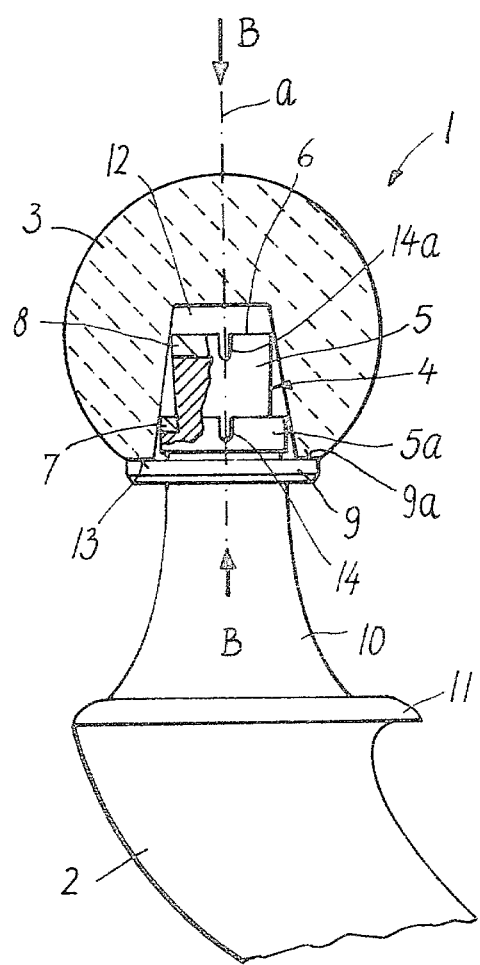

METAL-INFIBULUM CERAMIC-HEAD ENDOPROSTHESIS

BACKGROUND OF THE INVENTION

This invention relates to a hipbone endoprosthesis comprising an endomedullar infibulum made of a metal material which can be inserted into the medullar channel of the femur following removal of the femur epiphysis, and a spherical head made of a ceramic material which is associable with that portion of said infibulum protruding from the medullar channel.

With the adoption of ceramic materials for the spherical head construction, some considerable problems arise in connection with the rigid coupling of the infibulum to the spherical head. That coupling is in fact obtained by forming in the spherical head a frustoconical seat, wherein a complemantary portion of the infibulum is force fitted. The seat is individually formed in the spherical head, and a high degree of precision is required in its formation if an incorrect distribution of the loads is to be avoided which might result in the ceramic head being cracked, either while assembling the infibulum or during the prosthesis use, in view of the low tensile strength of ceramic materials.

SUMMARY OF THE INVENTION

This invention sets out to obviate the cited problems by providing a hipbone endoprosthesis wherein the infibulum-spherical head coupling ensures a correct distribution of the loads, and wherein the head machining only requires a moderate degree of precision and is easily and quickly carried out.

According to one aspect of this invention, there is provided a hipbone endoprosthesis comprising a metallic endomedullar infibulem insertable into the medullar channel of the femur, following removal of the femur epiphysis and having a portion protruding from said channel, and a spherical head made of a ceramic material, having a frustoconical cavity and force fit associable with said protruding portion wherein according to the improvement said protruding portion comprises a substantially cylindrical shank having a pair of axially extending annular ridges, having a saw-tooth cross-section with an outer substantially cylindrical face and an inner conical surface widening towards the end of said shank, said ridges having edges lying in a conical surface complementary to said cavity.

BRIEF DESCRIPTION OF THE DRAWING

Further features will be more clearly understood by making reference to the following description of a preferred embodiment of an endoprosthesis according to this invention, illustrated by way of example only in the accompanying drawing, where the one FIGURE shows a partly sectional side view of the endoprosthesis of this invention.

DESCRIPTION OF THE PREFERRED EMBODIMENTS

With reference to the drawing FIGURE, there is generally indicated at 1 a hipbone endoprosthesis according to this invention, which comprises an endomedullar infibulum 2 and spherical head 3. The infibulum is made of a metal material of the type comprising chromium-cobalt-molybdenum titanium alloys, and the head 3 is of a ceramic material. The infibulum comprises a shank 4, whereto the head 3 will be coupled, which has a substantially cylindrical shape including a reduced diameter portion 5 and a terminating end 6. One the end 6, and on the large diameter portion a conical surface complementary to of the shank, there are formed axially extending annular ridges 7 and 8 having a sawtooth cross-sectional configuration. The portion 5 is slightly tapered towards the large diameter portion 5a and the ridges have an outer substantially cylindrical surface and an inner conical surface which widens towards the end 6 with an angle which with respect to the axis a of the shank depends on the material from which the infibulum is formed, and is of approximately 30°.

The reference numeral 9 denotes a flange having a side 9a facing the shank 4. The flange 9 is connected by means of a portion 10 to a collar 11 intended for resting onto the severed femur or thigh bone. The portion 10 has a circular cross-section increasing from the flange 9 towards the collar 11.

The spherical head 3 comprises a cavity or recess 12 of frustoconical shape, the opening whereof is surrounded by ring bevelling 13 intended for resting onto the side 9a of the flange 9.

It should be noted that the ridges 7 and 8 are so spaced apart as to lay tangent to the wall of the cavity 12. In this way the edges of the ridges lie in a conical surface complementary to the cavity wall.

The spherical head 3 is secured to the infibulum by mutual force fitting (arrows B) under a preset load. It should be pointed out that said force fitting ensures that, when the flat ring bevelling 13 abuts against the flange 9 under a preset load, the machining of the frustoconical cavity 12 and ridges 7, 8 is correct. If abutting of the head 3 on the flange 9 does not occur, or occurs at a lower load than the preset one, this will be an indication that the machining mentioned above has been carried out incorrectly, thereby the coupling must be discarded. A first evaluation of the correctness of the machining operations is obtained when, after loosely inserting the shank 4 into the cavity 12 of the head, a preset gap is present between the flat ring bevelling 13 and side 9a.

The cited force fitting of the parts results in a deformation of the ridges 7 and 8; thus, the load will be distributed over the annular regions defined by the deformed ridges.

Advantageously, the ridges 7 and 8 have a series of radial cutouts, 14a to absorb thermal deformation of the shank during infibulum sterilization and to assure effectiveness of the coupling between the shank and head.

It should be noted that the invention, as described in the foregoing, requires no specially accurate machining of the frustonconical cavity 12. Furthermore, a control criterion on the effectiveness of the coupling is achieved automatically.

According to a variation of this invention, the number of the reduced diameter portions, and accordingly of the ridges 7 and 8, may differ from the number shown, and different may also be the angle which their inner surfaces form with the axis a.

I claim:
1. In a hipbone endoprosthesis comprising a metallic endomedullar infibulum insertable into the medullar channel of the femur, following removal of the femur epiphysis and having a portion protruding from said channel, and a spherical head made of a ceramic material, having a frustoconical cavity and force fit associable with said protruding portion, wherein the improve- ment comprises said protruding portion comprises a substantially cylindrical shank having a pair of axially extending annular ridges, said annular ridges having a saw-tooth cross-section with an outer substantially cylindrical surface and an inner conical surface widening towards the protuding end of said shank, said ridges having edges lying in a conical surface complementary to said cavity.

2. Hipbone endoprosthesis as claimed in claim 1 wherein said protruding portion includes a flange on which said ceramic head abuts and said shank is slightly tapered towards said flange.

3. Hipbone endoprosthesis as claimed in claim 1 wherein said ridges are provided with radial cutouts.

* * * * *